(12) United States Patent
Sansoucy

(10) Patent No.: US 10,143,822 B2
(45) Date of Patent: Dec. 4, 2018

(54) VALVED TIP CATHETERS

(75) Inventor: Michael Sansoucy, Wrentham, MA (US)

(73) Assignee: Covidien LP, Mansfield, MA (US)

( * ) Notice: Subject to any disclaimer, the term of this patent is extended or adjusted under 35 U.S.C. 154(b) by 1862 days.

(21) Appl. No.: 13/542,173

(22) Filed: Jul. 5, 2012

(65) Prior Publication Data
US 2014/0012209 A1    Jan. 9, 2014

(51) Int. Cl.
*A61M 25/00* (2006.01)
*A61M 1/36* (2006.01)

(52) U.S. Cl.
CPC ........ *A61M 25/003* (2013.01); *A61M 1/3661* (2014.02); *A61M 25/0075* (2013.01); *A61M 2025/0031* (2013.01); *A61M 2025/0076* (2013.01); *A61M 2025/0078* (2013.01)

(58) Field of Classification Search
CPC .............. A61M 25/003; A61M 1/3661; A61M 25/0075; A61M 2025/0031; A61M 2025/0076; A61M 2025/0078
See application file for complete search history.

(56) References Cited

U.S. PATENT DOCUMENTS

| | | | |
|---|---|---|---|
| 3,726,283 A * | 4/1973 | Dye ................. | A61M 25/0069 604/247 |
| 3,888,249 A * | 6/1975 | Spencer ............ | A61M 25/0021 604/247 |
| 4,391,276 A | 7/1983 | Lazarus et al. | |
| 4,403,983 A | 9/1983 | Edelman et al. | |
| 4,475,898 A | 10/1984 | Brodner et al. | |
| 4,493,696 A | 1/1985 | Uldall | |
| 4,549,879 A | 10/1985 | Groshong et al. | |
| 4,568,329 A | 2/1986 | Mahurkar | |
| 4,583,968 A | 4/1986 | Mahurkar | |
| 4,619,643 A | 10/1986 | Bai | |
| 4,626,240 A | 12/1986 | Edelman et al. | |
| 4,643,711 A | 2/1987 | Bates | |
| 4,671,796 A | 6/1987 | Groshong et al. | |
| 4,692,141 A | 9/1987 | Mahurkar | |
| 4,701,166 A | 10/1987 | Groshong et al. | |
| 4,753,640 A | 6/1988 | Nichols et al. | |
| 4,769,005 A | 9/1988 | Ginsburg et al. | |
| 4,772,268 A | 9/1988 | Bates | |
| 4,772,269 A | 9/1988 | Twardowski et al. | |
| 4,795,439 A | 1/1989 | Guest | |
| 4,801,297 A | 1/1989 | Mueller | |

(Continued)

FOREIGN PATENT DOCUMENTS

EP     0 299 622 A2    1/1989
EP     0 299 622 A3    1/1989
(Continued)

OTHER PUBLICATIONS

Office Action from Chinese Appl. No. 200910204452.0 dated Sep. 27, 2013.
(Continued)

*Primary Examiner* — Lauren P Farrar
(74) *Attorney, Agent, or Firm* — Kenneth Collier; Jessica Kwak Rauckman

(57) ABSTRACT

The present disclosure relates to multiple embodiments of catheters which include valved openings which are normally closed to maintain a lock solution within a catheter during periods of non-use.

19 Claims, 11 Drawing Sheets

(56) References Cited

U.S. PATENT DOCUMENTS

| | | |
|---|---|---|
| 4,808,155 A | 2/1989 | Mahurkar |
| 4,808,156 A | 2/1989 | Dean |
| 4,813,934 A | 3/1989 | Engelson et al. |
| 4,842,582 A | 6/1989 | Mahurkar |
| 4,895,561 A | 1/1990 | Mahurkar |
| 4,897,079 A | 1/1990 | Zaleski et al. |
| 4,961,809 A | 10/1990 | Martin |
| 4,973,319 A | 11/1990 | Melsky |
| 4,995,863 A | 2/1991 | Nichols et al. |
| 4,995,865 A | 2/1991 | Gahara et al. |
| 5,009,636 A | 4/1991 | Wortley et al. |
| 5,035,399 A | 7/1991 | Rantanen-Lee |
| 5,041,083 A | 8/1991 | Tsuchida et al. |
| 5,053,004 A | 10/1991 | Market et al. |
| 5,053,023 A | 10/1991 | Martin |
| 5,057,073 A | 10/1991 | Martin |
| 5,059,170 A | 10/1991 | Cameron |
| 5,085,632 A | 2/1992 | Ikada et al. |
| 5,106,368 A | 4/1992 | Uldall et al. |
| 5,112,301 A | 5/1992 | Fenton, Jr. et al. |
| 5,135,599 A | 8/1992 | Martin et al. |
| 5,147,332 A | 9/1992 | Moorehead |
| 5,156,592 A | 10/1992 | Martin et al. |
| 5,160,325 A | 11/1992 | Nichols et al. |
| 5,163,921 A | 11/1992 | Feiring |
| 5,167,623 A | 12/1992 | Cianci et al. |
| 5,171,218 A | 12/1992 | Fonger et al. |
| 5,188,593 A | 2/1993 | Martin |
| 5,190,520 A | 3/1993 | Fenton, Jr. et al. |
| 5,195,962 A | 3/1993 | Martin et al. |
| 5,197,951 A | 3/1993 | Mahurkar |
| 5,209,723 A | 5/1993 | Twardowski et al. |
| 5,219,335 A | 6/1993 | Willard et al. |
| 5,221,255 A | 6/1993 | Mahurkar et al. |
| 5,221,256 A | 6/1993 | Mahurkar |
| 5,224,938 A | 7/1993 | Fenton, Jr. |
| 5,250,034 A | 10/1993 | Appling et al. |
| 5,261,885 A | 11/1993 | Lui |
| 5,267,979 A | 12/1993 | Appling et al. |
| 5,269,768 A | 12/1993 | Cheung |
| 5,304,155 A | 4/1994 | Lui |
| 5,308,338 A | 5/1994 | Helfrich |
| 5,318,536 A | 6/1994 | Williams |
| 5,346,471 A | 9/1994 | Raulerson |
| 5,348,536 A | 9/1994 | Young et al. |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,395,316 A | 3/1995 | Martin |
| 5,399,172 A | 3/1995 | Martin et al. |
| 5,403,291 A | 4/1995 | Abrahamson |
| 5,405,341 A | 4/1995 | Martin |
| 5,451,206 A | 9/1995 | Young |
| 5,464,398 A | 11/1995 | Haindl |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,522,807 A | 6/1996 | Luther |
| 5,531,679 A | 7/1996 | Schulman et al. |
| 5,554,136 A | 9/1996 | Luther |
| 5,556,390 A | 9/1996 | Hicks |
| 5,569,182 A | 10/1996 | Twardowski et al. |
| 5,571,093 A | 11/1996 | Cruz et al. |
| D381,420 S | 7/1997 | Musgrave et al. |
| D384,411 S | 9/1997 | Musgrave et al. |
| D384,741 S | 10/1997 | Musgrave et al. |
| 5,683,640 A | 11/1997 | Miller et al. |
| 5,685,867 A | 11/1997 | Twardowski et al. |
| 5,702,365 A | 12/1997 | King |
| 5,718,678 A | 2/1998 | Fleming, III |
| 5,776,096 A | 7/1998 | Fields |
| 5,797,869 A | 8/1998 | Martin et al. |
| 5,807,311 A | 9/1998 | Palestrant |
| 5,807,329 A | 9/1998 | Gelman |
| 5,807,349 A | 9/1998 | Person et al. |
| 5,810,789 A | 9/1998 | Powers et al. |
| 5,830,184 A | 11/1998 | Basta |
| 5,830,196 A | 11/1998 | Hicks |
| 5,868,717 A | 2/1999 | Prosl |
| 5,928,203 A | 7/1999 | Davey et al. |
| 5,947,953 A | 9/1999 | Ash et al. |
| 5,961,485 A | 10/1999 | Martin |
| 5,961,486 A | 10/1999 | Twardowski et al. |
| 5,968,009 A | 10/1999 | Siman |
| 5,976,103 A | 11/1999 | Martin |
| 5,984,903 A | 11/1999 | Nadal |
| 5,989,206 A | 11/1999 | Prosl et al. |
| 5,989,213 A | 11/1999 | Maginot |
| 5,993,437 A | 11/1999 | Raoz |
| 6,001,079 A | 12/1999 | Pourchez |
| 6,004,310 A | 12/1999 | Bardsley et al. |
| 6,099,519 A | 8/2000 | Olsen et al. |
| 6,123,725 A | 9/2000 | Aboul-Hosn |
| 6,126,631 A | 10/2000 | Loggie |
| 6,146,354 A | 11/2000 | Beil |
| 6,156,016 A | 12/2000 | Maginot |
| 6,190,349 B1 | 2/2001 | Ash et al. |
| 6,190,371 B1 | 2/2001 | Maginot et al. |
| 6,206,849 B1 | 3/2001 | Martin et al. |
| 6,273,875 B1 | 8/2001 | Siman et al. |
| 6,280,423 B1 | 8/2001 | Davey et al. |
| 6,293,927 B1 | 9/2001 | McGuckin, Jr. |
| 6,293,958 B1 | 9/2001 | Berry et al. |
| 6,342,120 B1 | 1/2002 | Basta |
| 6,346,090 B1 | 2/2002 | Liska et al. |
| 6,394,141 B2 | 5/2002 | Wages et al. |
| 6,409,700 B1 | 6/2002 | Siegel, Jr. et al. |
| 6,447,488 B2 | 9/2002 | Estabrook et al. |
| 6,461,321 B1 | 10/2002 | Quinn |
| 6,475,207 B1 | 11/2002 | Maginot et al. |
| 6,482,169 B1 | 11/2002 | Kuhle |
| 6,506,182 B2 | 1/2003 | Estabrook et al. |
| 6,579,261 B1 | 6/2003 | Kawamura |
| 6,585,705 B1 | 7/2003 | Maginot et al. |
| 6,592,542 B2 | 7/2003 | Childers et al. |
| 6,592,558 B2 | 7/2003 | Quah |
| 6,595,966 B2 | 7/2003 | Davey et al. |
| 6,620,118 B1 | 9/2003 | Prosl et al. |
| 6,638,242 B2 | 10/2003 | Wilson et al. |
| 6,692,473 B2 | 2/2004 | St. Cyr et al. |
| 6,695,832 B2 | 2/2004 | Schon et al. |
| 6,719,749 B1 | 4/2004 | Schweikert et al. |
| 6,723,084 B1 | 4/2004 | Maginot et al. |
| 6,730,096 B2 | 5/2004 | Basta |
| 6,743,218 B2 | 6/2004 | Maginot et al. |
| 6,749,580 B2 | 6/2004 | Work et al. |
| 6,758,836 B2 | 7/2004 | Zawacki |
| 6,786,884 B1 | 9/2004 | DeCant, Jr. et al. |
| 6,808,510 B1 | 10/2004 | DiFiore |
| 6,814,718 B2 | 11/2004 | McGuckin, Jr. et al. |
| 6,858,019 B2 | 2/2005 | McGuckin, Jr. et al. |
| 6,872,198 B1 | 3/2005 | Wilson et al. |
| 6,886,752 B2 | 5/2005 | Murayama et al. |
| 6,911,014 B2 | 6/2005 | Wentling et al. |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,966,886 B2 | 11/2005 | Appling |
| 6,969,381 B2 | 11/2005 | Voorhees |
| 6,976,973 B1 | 12/2005 | Ruddell et al. |
| 6,986,752 B2 | 1/2006 | McGuckin, Jr. et al. |
| 6,991,625 B1 | 1/2006 | Gately et al. |
| 7,008,395 B2 | 3/2006 | Loggie |
| 7,008,412 B2 | 3/2006 | Maginot |
| 7,011,645 B2 | 3/2006 | McGuckin, Jr. et al. |
| 7,013,928 B2 | 3/2006 | Navis |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,182,746 B2 | 2/2007 | Haarala et al. |

(56) References Cited

U.S. PATENT DOCUMENTS

| | | |
|---|---|---|
| 7,413,564 B2 | 8/2008 | Morris et al. |
| 8,747,343 B2 | 6/2014 | MacMeans et al. |
| 8,986,263 B2 | 3/2015 | Tanaka et al. |
| 9,005,154 B2 | 4/2015 | Matson et al. |
| 9,044,576 B2 | 6/2015 | Onuma |
| 2002/0090339 A1 | 7/2002 | Whalen et al. |
| 2002/0121282 A1 | 9/2002 | McGuskin, Jr. et al. |
| 2002/0156430 A1 | 10/2002 | Haarala |
| 2002/0165492 A1 | 11/2002 | Davey et al. |
| 2003/0032918 A1 | 2/2003 | Quinn |
| 2003/0093028 A1 | 5/2003 | McGuckin, Jr. et al. |
| 2003/0093029 A1 | 5/2003 | McGuckin, Jr. et al. |
| 2003/0165492 A1 | 9/2003 | Panerai |
| 2003/0191425 A1 | 10/2003 | Rosenblatt |
| 2004/0176743 A1 | 9/2004 | Morris et al. |
| 2004/0249337 A1 | 12/2004 | DiFiore |
| 2005/0027261 A1 | 2/2005 | Weaver et al. |
| 2005/0033222 A1 | 2/2005 | Haggstrom et al. |
| 2005/0085765 A1 | 4/2005 | Voorhees |
| 2005/0090776 A1 | 4/2005 | McGuckin, Jr. et al. |
| 2005/0215978 A1 | 9/2005 | Ash |
| 2005/0228339 A1 | 10/2005 | Clark |
| 2005/0256509 A1 | 11/2005 | Sakai |
| 2005/0267400 A1 | 12/2005 | Haarala et al. |
| 2005/0277862 A1 | 12/2005 | Anand |
| 2005/0288623 A1 | 12/2005 | Hjalmarsson |
| 2006/0004325 A1 | 1/2006 | Hamatake et al. |
| 2006/0149191 A1 | 7/2006 | DiFiore |
| 2006/0184089 A1* | 8/2006 | Makower .......... A61B 17/00234 604/9 |
| 2006/0253063 A1 | 11/2006 | Schweikert |
| 2007/0100298 A1 | 5/2007 | Appling |
| 2007/0225678 A1 | 9/2007 | Lui |
| 2007/0225682 A1* | 9/2007 | Ash ...................... A61M 25/003 604/532 |
| 2009/0054825 A1 | 2/2009 | Melsheimer et al. |
| 2009/0312718 A1 | 12/2009 | Onuma |
| 2010/0069818 A1 | 3/2010 | Smouse |
| 2010/0081986 A1* | 4/2010 | Matson ............... A61M 25/003 604/6.16 |
| 2011/0130745 A1 | 6/2011 | Shevgoor et al. |
| 2013/0085478 A1* | 4/2013 | Malhi ................. A61M 1/3653 604/523 |
| 2015/0250938 A1 | 9/2015 | Matson et al. |

FOREIGN PATENT DOCUMENTS

| | | |
|---|---|---|
| EP | 0 554 722 A1 | 8/1993 |
| EP | 0 322 225 B1 | 2/1995 |
| EP | 0 713 406 B1 | 3/1998 |
| EP | 0 864 336 A3 | 3/1999 |
| EP | 0 570 530 B1 | 8/1999 |
| EP | 0 555 780 B1 | 9/1999 |
| EP | 1 595 565 A | 11/2005 |
| EP | 1 144 039 B1 | 12/2005 |
| EP | 1955728 A1 | 8/2008 |
| EP | 2 119 468 A1 | 11/2009 |
| EP | 2 168 625 | 3/2010 |
| EP | 2168625 A1 | 3/2010 |
| JP | 2006015058 A | 1/2006 |
| JP | 2007-175297 | 7/2007 |
| JP | 2008-126661 | 6/2008 |
| WO | 92/22342 A1 | 12/1992 |
| WO | 9318814 A1 | 9/1993 |
| WO | WO 95/04567 A1 | 2/1995 |
| WO | WO 97/37699 A1 | 10/1997 |
| WO | WO 98/41277 | 9/1998 |
| WO | WO 99/016493 | 4/1999 |
| WO | WO 99/38550 | 8/1999 |
| WO | WO 99/65557 | 12/1999 |
| WO | WO 00/06239 A2 | 2/2000 |
| WO | 00/056387 A1 | 9/2000 |
| WO | WO 01/91845 A1 | 12/2001 |
| WO | WO 02/13899 A1 | 2/2002 |
| WO | WO 02/018004 A3 | 3/2002 |
| WO | WO 03/033049 A3 | 4/2003 |
| WO | WO 03/066148 A1 | 8/2003 |
| WO | WO 2004/093956 A1 | 11/2004 |
| WO | WO 2005/023336 A2 | 3/2005 |
| WO | WO 2005/077449 A1 | 8/2005 |
| WO | WO 2005/084741 A1 | 9/2005 |
| WO | WO 2006/014339 A2 | 2/2006 |
| WO | 2006/122026 A2 | 11/2006 |
| WO | WO 2007/111874 A2 | 10/2007 |

OTHER PUBLICATIONS

Office Action issued in Japanese Application No. 2013-137993 dated May 1, 2014.

Patent Examination Report No. 1 issued in Australian Appl. No. 2013206662 dated Jun. 27, 2014.

Examiner's Report issued in Canadian Application No. 2,820,412 dated Jul. 17, 2014.

Notification of the First Office Action, and translation thereof, from counterpart Chinese Patent Application No. 201310280523.1, dated May 18, 2015, 12 pp.

EP Search Report from EP Application No. EP 12 18 4656 dated May 11, 2012.

Extended European Search Report corresponding to EP Application No. 09 17 0662, completed Jan. 11, 2010; completed on Jan. 11, 2010 (3 pages).

Extended European Search Report issued by the European Patent Office and completed on Sep. 22, 2009 in co-pending European Patent Application No. EP 09251289.6.

Extended European Search Report issued by the European Patent Office dated May 21, 2012 in EP Application No. 12158534.

Australian Office Action dated Sep. 14, 2012 issued in copending Australian Application No. 2012201416.

Second Office Action, and translation thereof, counterpart Chinese Application No. 201310280523.1, dated Oct. 22, 2015, 5 pp.

Communication pursuant to Article 94(3) EPC from counterpart European Application No. 13173513.6, dated Nov. 4, 2016, 4 pp.

Trerotola et al., "Randomized comparison of split tip versus step tip high-flow hemodialysis catheters," Kidney International, International Society of Nephrology, vol. 62, Jul. 2002, 9 pp.

Examination Report from counterpart European Application No. 13173513.6, dated Sep. 25, 2018, 6 pp.

* cited by examiner

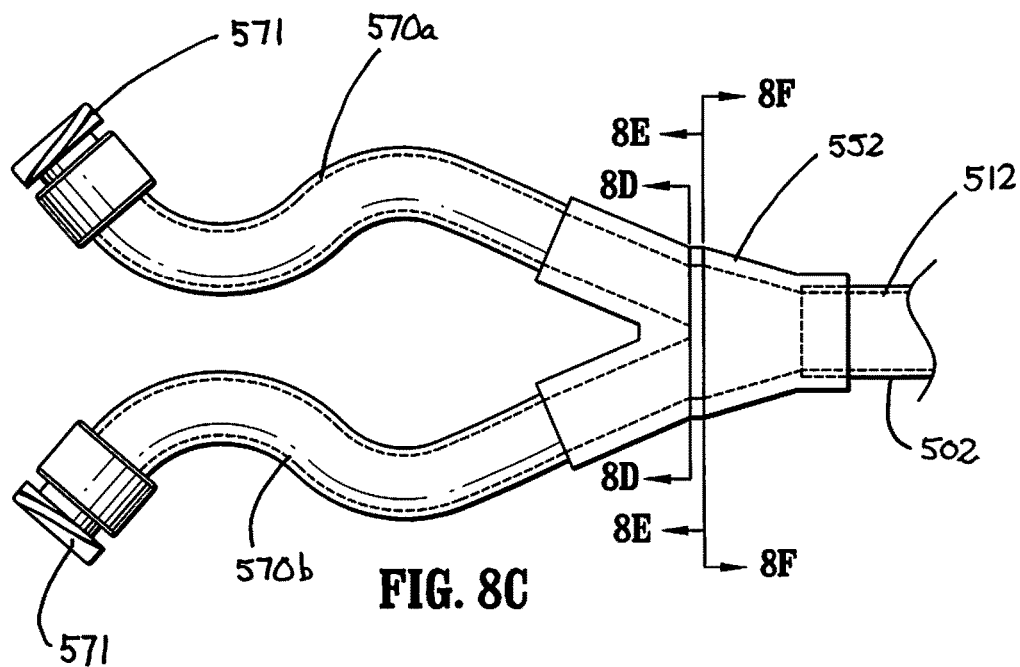
FIG. 8C
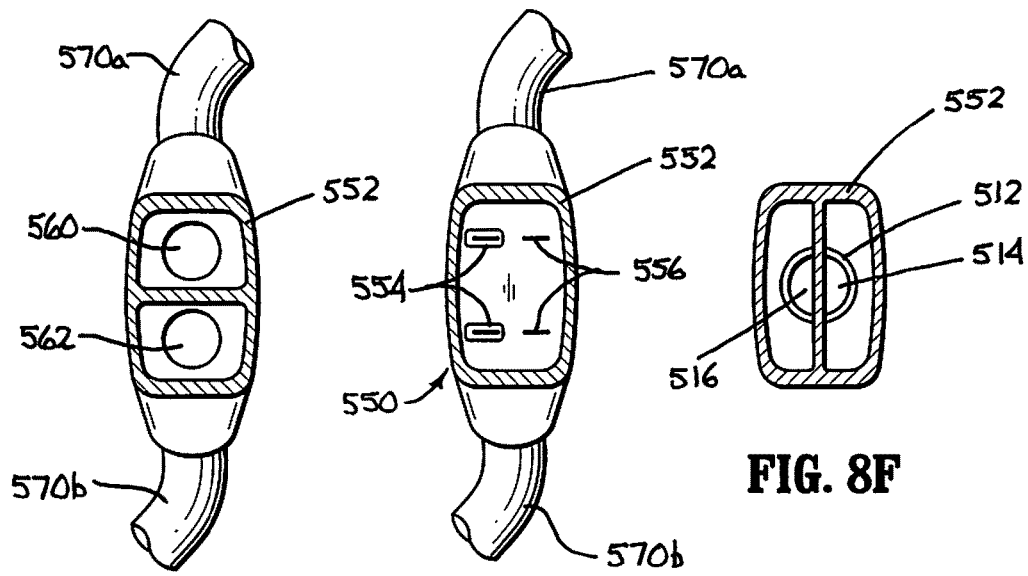
FIG. 8D   FIG. 8E   FIG. 8F

VALVED TIP CATHETERS

TECHNICAL FIELD

The present disclosure relates to medical catheters and in particular, to medical catheters defining at least one valved opening.

BACKGROUND

Catheters are flexible medical instruments for use in the introduction and withdrawal of fluids to and from body cavities, ducts and vessels. Catheters are used for many different applications within the human body including the administration of liquid therapeutic agents and the removal of bodily fluids for testing, monitoring, treatment or disposal. Catheters have a particular application in hemodialysis procedures, in which blood is withdrawn from a blood vessel, directed to a hemodialysis unit for dialysis or purification, and subsequently returned to the blood vessel.

Typically, chronic catheters remain implanted within the body for extended periods of time. Because of this, clotting and thrombus formation within the catheter lumen or lumens can be problematic. To minimize the potential problems which may result from thrombus formation within the catheter lumen(s), it is common to "lock" the catheter during periods of non-use, such as an interdialytic period. Locking typically involves flushing the catheter with saline to remove blood and other fluids from the catheter lumen(s) and injecting an anticoagulant solution, for example, heparin, into the catheter to fill the lumen(s). The anticoagulant solution displaces any blood that may remain in the lumen(s) and actively inhibits thrombus formation within the lumen(s) of the catheter.

One problem associated with known catheters is that during periods of non-use, such as the interdialytic period, the anticoagulant in the distal end of the catheter lumen tends to partially drain from the lumen such that blood is able to enter the distal end of the catheter. This stagnant blood within the distal end of the catheter results in thrombus formation at the distal end of the catheter lumen.

It would be desirable to provide a catheter that is configured to retain an anticoagulant within the catheter lumen(s) during the periods of non-use to prevent thrombus formation within the catheter. It would also be desirable to provide a catheter that is configured to prevent the inflow of blood into the catheter lumen(s) during periods of non-use to prevent thrombosis formation without the use of a locking solution, such as heparin.

SUMMARY

A catheter is disclosed which includes a body defining first and second lumens and at least one distally located normally closed, one-way valve associated with each of the first and second lumens. Each of the distally located one-way valves is configured to open in response to an increase in pressure within a respective one of the first and second lumens to enable fluid to be discharged from the respective first or second lumen. The catheter also includes at least one proximally located normally closed, one-way valve associated with each of the first and second lumens. Each of the proximally located one-way valves is spaced proximally of the distally located one-way valves and is configured to open in response to a decrease in pressure within a respective one of the first and second lumens to enable fluid to enter the respective first or second lumen.

In one embodiment, each of the distally located one-way valves and each of the proximally located one-way valves is a slit valve.

The catheter may include support structure formed in the body adjacent at least one of the proximally located one-way valves.

In one embodiment, each of the proximally located one-way valves includes tapered inwardly deformable flaps. Alternatively, each of the proximally located one-way valves may include a slit which extends through the body and includes a concavity formed about the slit. In yet another embodiment, the proximally located one-way valves may include a flap valve including a deformable flap. The deformable flap can be rectangular, triangular or assume any of a variety of other configurations.

In one embodiment, each of the proximally located one-way valves is a duckbill valve.

In another embodiment, the body comprises separated tip portions wherein each of the separated tip portions includes at least one of the distally located one-way valves and/or at least one of the proximally located one-way valves. Alternatively, the proximally located one-way valves may be formed in the body proximally of the separated tip portions.

In one embodiment, each of the proximally located one-way valves includes a membrane supported within the respective one of the first and second lumens of the body. The membrane is positioned to cover a throughbore fat lied in the body and is inwardly movable to enable fluid to enter the throughbore. At least a portion of the membrane is secured to the body. A support rib may be provided to extend across the throughbore to prevent outward movement of the membrane.

A catheter assembly is also disclosed which includes a catheter including a body defining a venous lumen and an arterial lumen wherein a distal end of the venous lumen extends distally beyond a distal end of the arterial lumen. A one-way valve is formed in the distal end of the venous lumen and is configured to enable fluid to be discharged from the venous lumen upon an increase in pressure within the venous lumen. A one-way valve is also formed in the distal end of the arterial lumen and is configured to enable fluid to enter the arterial lumen upon a decrease in pressure within the arterial lumen.

In one embodiment, a catheter hub is secured to a proximal end of the catheter body. The catheter hub supports a valve assembly having two inlet one-way valves which communicate with the venous lumen and enable fluid to flow into the venous lumen and two outlet one-way valves which communicate with the arterial lumen and enable fluid to flow from the arterial lumen. A conduit adapted to communicate with a medical device defines first and second lumens and has a first end connected to the catheter hub such that each of the first and second lumens communicate with one of the inlet one-way valves and one of the outlet one-way valves.

A catheter is also disclosed which comprises a body defining at least one lumen including a proximal body portion and a distal body portion. The distal body portion is formed of an elastomeric material including at least one perforation. The distal portion is stretchable from a first unbiased state wherein the at least one perforation is sealed to a second biased state wherein the at least one perforation defines an opening. A push rod is supported within the catheter body and is movable from a retracted position to an advanced position to move the distal portion from its unbiased state to its biased state. In one embodiment, the catheter body includes a channel dimensioned to slidably receive the push rod. The channel includes a closed distal end positioned to engage a distal end of the push rod.

A catheter is also disclosed which comprises a body defining first and second lumens, and at least one distally located normally closed, one-way valve in fluid communication with at least one of the first and second lumens. Each of the distally located one-way valves being configured to open in response to an increase in pressure within the respective first and second lumens to which the distally located one-way valve is in fluid communication to enable fluid to be discharged from the respective first or second lumen. At least one proximally located normally closed, one-way valve is also in fluid communication with at least one of the first and second lumens. Each of the proximally located one-way valves is spaced proximally of the distally located one-way valves and is configured to open in response to a decrease in pressure within the respective first and second lumens to which the proximally located one-way valve is in fluid communication to enable fluid to enter the respective first or second lumen.

BRIEF DESCRIPTION OF THE DRAWINGS

Various embodiments of the presently disclosed valved tip catheter will be described herein with reference to the accompanying drawings, wherein:

FIG. 8C is a top view of the proximal end of the catheter shown in FIG. 8A in association with a hub member and extension tubes for communicating with a medical device;

FIG. 8D is a cross-sectional view taken along section lines 8D-8D of FIG. 8C;

FIG. 8E is a cross-sectional view taken along section lines 8E-8E of FIG. 8C;

FIG. 8F is a cross-sectional view taken along section lines 8F-8F of FIG. 8C;

DETAILED DESCRIPTION OF EMBODIMENTS

Various exemplary embodiments of the presently disclosed catheter are discussed herein in terms of a hemodialysis catheter. However, it is envisioned that the principles of the present disclosure are equally applicable to a range of catheter applications such as, for example, cardiac, abdominal, urinary, and intestinal, including both chronic and acute applications. Moreover, the catheter can be used for the delivery and/or withdrawal of fluids such as, for example, medication, saline, bodily fluids, blood and urine.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human patient or other animal, and the term "clinician" should be understood as referring to a doctor, nurse or other care provider and may include support personnel.

Figure 1:
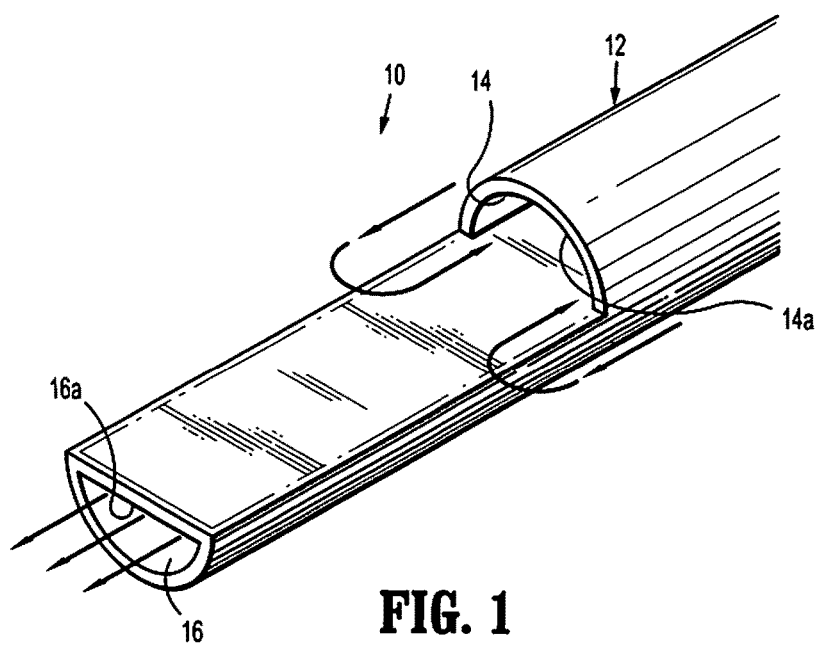
FIG. 1 is a perspective view of a prior art dual lumen catheter having a separated tip configuration.

FIG. 1 illustrates the distal end of a prior art catheter shown generally as 10. Catheter 10 is a dual lumen catheter and includes a body 12 defining an arterial lumen 14 and a venous lumen 16. The portion of body 12 defining the venous lumen 16 extends distally of the portion of the body 12 defining the arterial lumen 14 such that a distal opening 14a of the arterial lumen 14 is positioned proximally of a distal opening 16a of the venous lumen 16.

In use, blood is withdrawn from a patient through the arterial lumen 14 and delivered to a dialyzer (not shown) wherein toxins are removed from the blood. Thereafter, the blood is returned to the patient through the venous lumen 16. The spacing between the distal opening 14a of the arterial lumen 14 and the distal opening 16a of the venous lumen 16 minimizes the degree of recirculation of blood within the catheter. As used herein, "recirculation" is defined as the flow of purified blood exiting the venous lumen 16 directly into the arterial lumen 14.

During periods of non-use, such as the period between dialysis treatments, a lock solution or anticoagulant, such as heparin, is typically injected into the arterial and venous lumens 14 and 16 to prevent thrombus formation. Because the catheter body 12 defines arterial and venous lumens 14 and 16 which have open ends 14a and 16a, respectively, in fluid communication with flowing blood in a bloodstream, the lock solution has a tendency to leak from the distal end of the arterial and venous lumens 14 and 16. When this occurs, blood is able to flow into and stagnate within the distal end of the arterial and venous lumens 14 and 16. This commonly results in the formation of thrombosis which may partially or completely occlude blood flow to or from the catheter 10. Because the venous lumen 16 extends distally of the arterial lumen 14, the flow cannot be reversed by switching the communication of the arterial and venous lumens with the dialyzer, to potentially dislodge the thrombosis, without greatly increasing recirculation. Yet further, thrombus is expensive to treat once it has formed. Treatment of thrombus by flushing the catheter with heparinized saline is typically insufficient. Tissue plasminogen activator (tPA) is generally employed to dissolve the thrombus. However, each use of tPA is very expensive. More importantly, however, thrombus can lead to failure of the catheter requiring catheter removal and all the inherent concerns associated with catheter removal, such as patient discomfort, potential for infection and/or scarring, etc.

Figure 2:
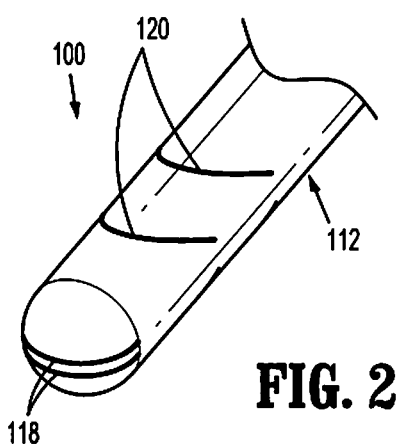
FIG. 2 is a perspective view of the distal end of one embodiment of the presently disclosed valved tip catheter prior to use.
Figure 3:
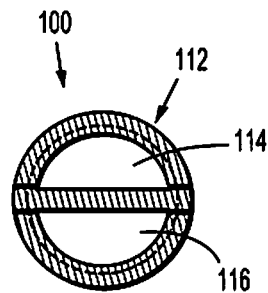
FIG. 3 is a cross-sectional view taken along section-lines 3-3 of FIG. 3A.
Figure 3A:
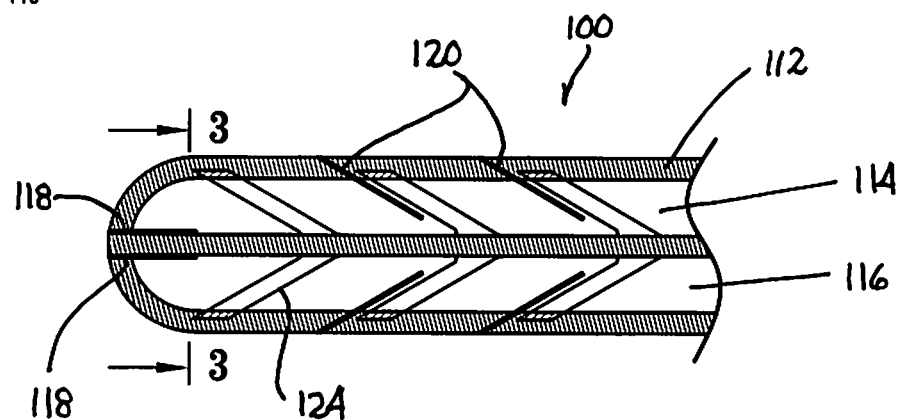
FIG. 3A is a cross-sectional view of the valved tip catheter shown in FIG. 2.
Figure 3B:
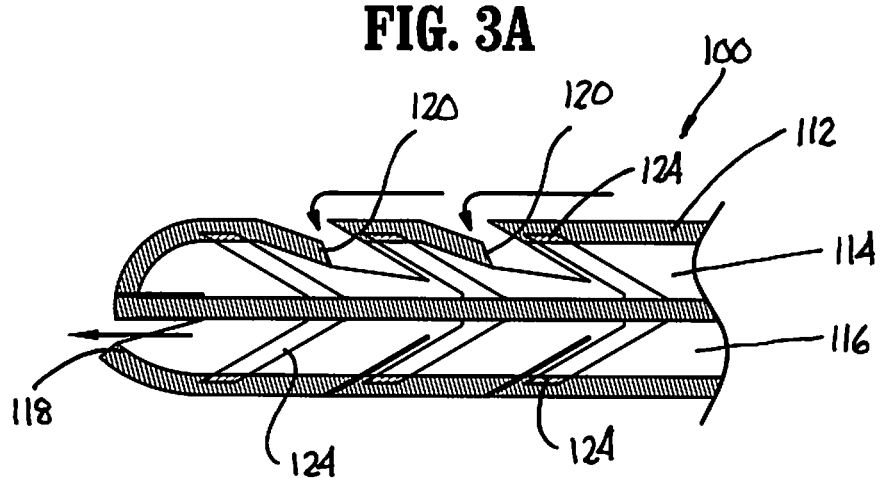
FIG. 3B is a cross-sectional view of the valved tip catheter shown in FIG. 2 in use.

FIGS. 2-3B illustrate one embodiment of the presently disclosed catheter comprising a valved tip, which is shown generally as 100. Catheter 100 includes a body 112 which defines first and second lumens 114 and 116. Unlike prior art catheter 10, the catheter 100 is reversible such that either one of the first and second lumens 114 and 116 can function as the arterial lumen or the venous lumen as will be discussed in further detail below. The body 112 defines at least two distal one-way valves 118 and at least two proximal one-way valves 120. More specifically, at a minimum, one distal one-way valve 118 and one proximal one-way valve 120 are employed for each catheter lumen 114 and 116. Each of the distal and proximal one-way valves 118 and 120, respectively, are normally closed and extend through outer walls of the catheter body 112 along an axis transverse to the longitudinal axis of the catheter body 112. At least one of the distal one-way valves 118 and at least one of the proximal one-way valves 120 communicates with each of the first and second body lumens 114 and 116. The distal one-way valves 118 are configured to open outwardly in response to an increase in pressure within a respective lumen 114 or 116 to enable fluid to exit the first or second body lumen 114 or 116 (FIG. 3B). In contrast, the proximal one-way valves 120 are configured to open inwardly in response to a decrease in pressure within a respective lumen to enable fluid to enter the first or the second body lumen 114 or 116. While the pressure differentials have been described as increases and decreases in pressure within the lumens, any pressure differential between the lumen and the exterior environment of the catheter may be used to open or close the valves 118, 120. Although two distal one-way valves 118 and four proximal one-way valves 120 are illustrated, it is envisioned that two or more distal and proximal one-way valves can be provided in body 112. For example, the body 112 may have four distal valves 118 and six proximal valves 120 or two distal valves 118 and two proximal valves 120. The number and sizes of the valves 118, 120 may be configured to enable the desired flow rates through the catheter 100. Also, the first lumen 114 may include a single distal one-way valve 118 only and the second lumen may include a single proximal one-way valve 120 only. However, such an embodiment would not be reversible.

Figure 3C:
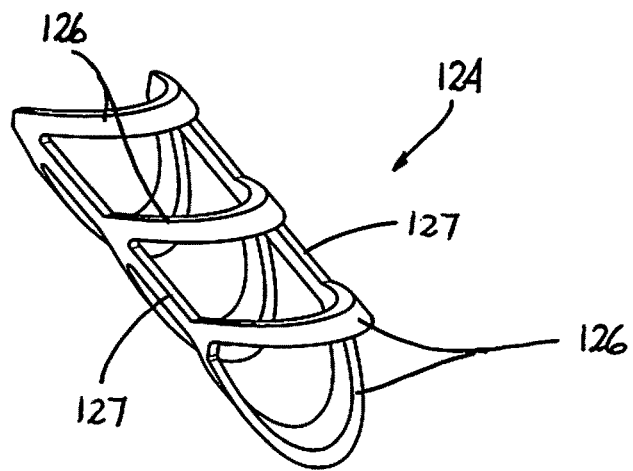
FIG. 3C is a perspective view of the support structure of the valved tip catheter shown in FIG. 2.
Figure 3D:
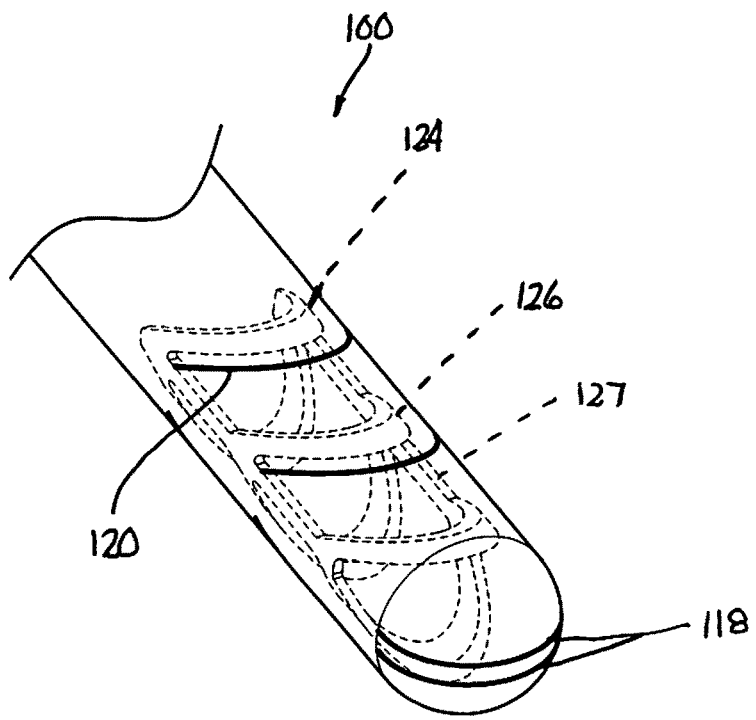
FIG. 3D is a perspective view of the distal end of the valved tip catheter shown in FIG. 2 with support structure shown in phantom.

As illustrated in FIGS. 3A-3D, the distal and proximal valves 118 and 120 can be formed as slit valves. Alternately, other valve configurations are envisioned. The body 112 may also include internal support structure 124 to support the proximal valves 120 and prevent the lumens 114 and 116 from collapsing in the area adjacent to the proximal valves 120 (FIGS. 3C and 3D). The support structure 124 may include a skeletal system defined by curved or arcuate ribs 126 which are positioned adjacent to each of proximal valves 120. In one embodiment, ribs 126 extend between longitudinal supports 127 and are angled in a distal direction (FIG. 3C). In one embodiment, the support structure 124 is formed from a material which is more rigid than the material used to form body 112 and the body 112 is overmolded about support structure 124. Alternately, other methods of construction are envisioned.

In use, when proximal end of the catheter 100 is connected to a dialyzer such that fluid is withdrawn through the first lumen 114 and supplied through the second lumen 116, the distal one-way valve 118 communicating with the second lumen 116 will open outwardly (FIG. 3B) to enable fluid F to be discharged from the distal end of the second lumen 116 and the proximal one-way valves 120 communicating with the first lumen 114 will open inwardly (FIG. 3B) to enable fluid F to enter catheter 100 through the proximal one-way valves 120.

As discussed above, catheter 100 is reversible. Thus, if catheter 100 is connected to a dialyzer such that fluid is withdrawn through the second lumen 116 and supplied through the first lumen 114, the distal one-way valve 118 communicating with the first lumen 114 will open outwardly to enable fluid to exit the distal end of the first lumen 114 and the proximal one-way valves 120 communicating with the second lumen 116 will open inwardly to enable fluid to enter the second lumen 116 through the proximal valves 120.

Because of the configuration of the catheter 100 and the positioning of the distal and proximal one-way valves 118, 120 in relation to each other, the catheter 100 provides a catheter with spaced inflow and outflow streams to minimize recirculation. The normally closed distal and proximal valves 118 and 120 also provide a sealed structure to retain a lock solution, such as an anticoagulant, within the catheter 100 during periods of non-use. In addition, because catheter 100 is also reversible, a clinician cannot improperly connect the catheter 100 to a medical device such as a dialyzer.

Figure 4:
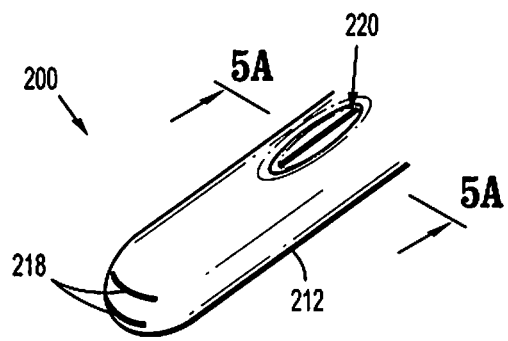
FIG. 4 is a perspective view of another embodiment of the presently disclosed valved tip catheter.
Figure 5A:
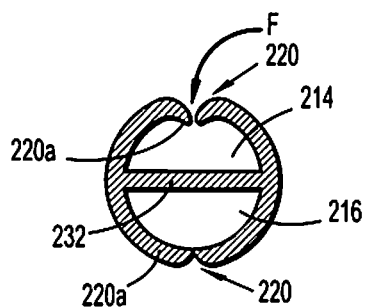
FIG. 5A is a cross-sectional view taken along section lines 5A-5A of FIG. 4 during use of the catheter.
Figure 5B:
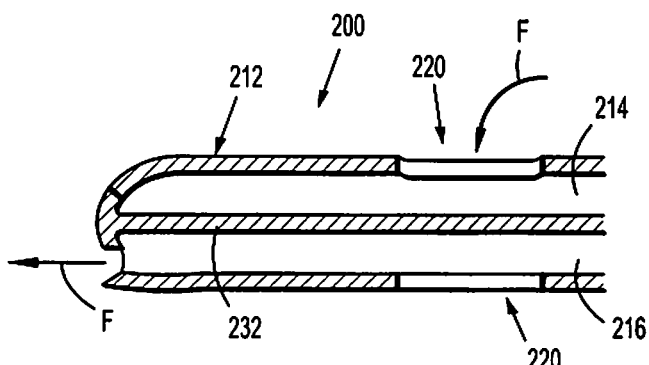
FIG. 5B is a longitudinal cross-sectional view of the catheter shown in FIG. 4 during use of the catheter.

FIGS. 4-5B illustrate another embodiment of the presently disclosed catheter which is shown generally as catheter 200. Catheter 200 is similar to catheter 100 and includes a body 212 defining first and second lumens 214 and 216 separated by a septum 232, and at least two distal one-way slit valves 218. Catheter body 212 also defines at least two proximal one-way slit valves 220 which include tapered inwardly deformable flaps 220a. Catheter 200 differs from catheter 100 discussed above in that proximal one-way slit valves 220 define slits which extend along an axis which is parallel to the longitudinal axis of the catheter body 212, wherein the slits are defined by the tapered flaps 220a. As shown in FIGS. 5A and 5B, distal one-way valves 218 are normally closed and open outwardly to enable fluid F to exit a respective lumen 214 or 216 and proximal one-way valves 220 are normally closed and open inwardly to enable fluid F to enter a respective lumen 214 or 216. As discussed above with respect to catheter 100, the distal and proximal valves 218 and 220 are spaced to minimize recirculation, and are normally closed to retain a lock solution such as an anticoagulant within the catheter lumens during periods of non-use. In addition, since each lumen 214 and 216 communicates with at least one distal one-way valve 218 and at least one proximal one-way valve 220, catheter 200 is also reversible.

Figure 6:
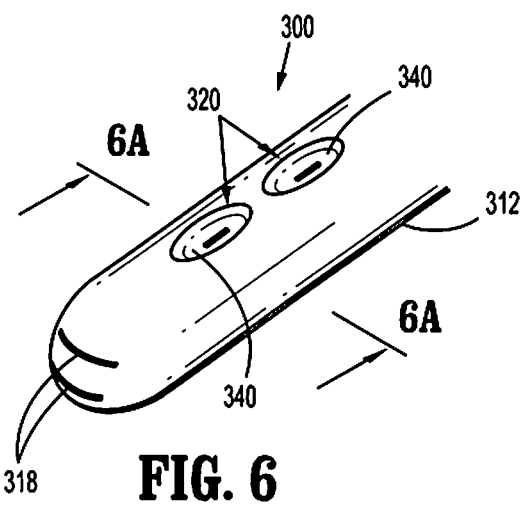
FIG. 6 is a perspective view of another embodiment of the presently disclosed valved tip catheter prior to use.
Figures 6A, 6B:
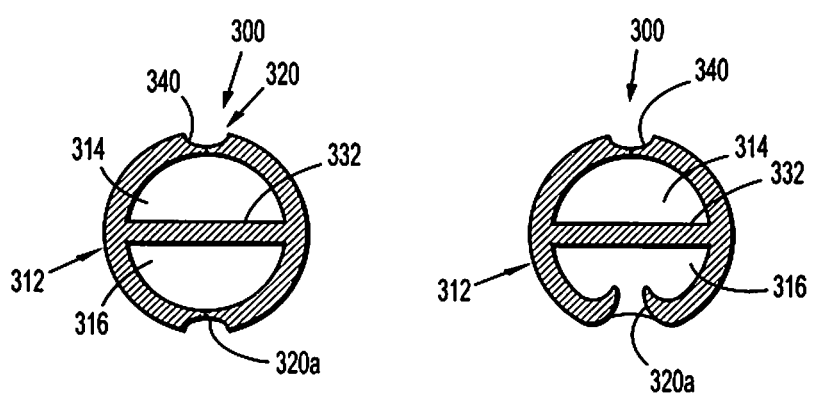
FIG. 6A is a cross-sectional view taken along section lines 6A-6A of FIG. 6.
FIG. 6B is a cross-sectional view of the catheter shown in FIG. 6 in use.

FIGS. 6-6B illustrate another embodiment of the presently disclosed catheter shown generally as catheter 300. Catheter 300 is substantially similar to catheter 200 and includes a body 312 which defines first and second lumens 314 and 316 separated by a septum 332, at least two distal one-way slit valves 318, and at least two proximal one-way slit valves 320. Proximal slit valves 320 define slits which extend parallel to the longitudinal axis of catheter body 312. In contrast to catheter 200, catheter 300 includes a concavity 340 which is formed about each slit valve 320. By providing concavities 340 about slit valves 320, the thickness of a deformable portion 320a of proximal valves 320 is reduced to enable the proximal valves 320 to open more easily. Such a concavity may be beneficial depending upon the rigidity of the material used to construct the catheter.

Figure 7:
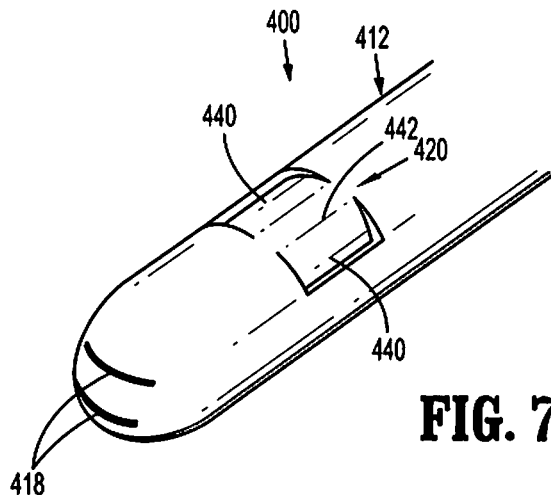
FIG. 7 is a perspective view of another embodiment of the presently disclosed valved tip catheter.
Figure 7A:
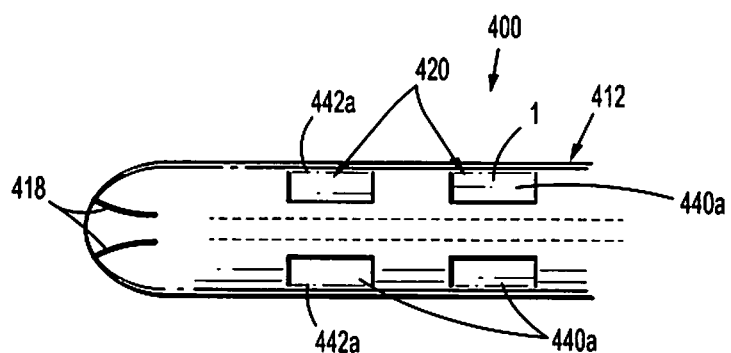
FIG. 7A is a top view of another embodiment of the presently disclosed valved tip catheter.
Figure 7B:
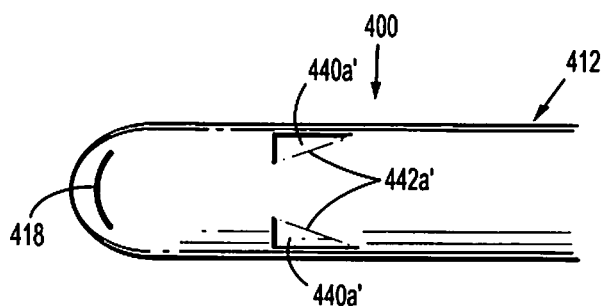
FIG. 7B is a top view of another embodiment of the presently disclosed valved tip catheter.

FIGS. 7-7A illustrate another embodiment of the presently disclosed catheter shown generally as catheter 400. Catheter 400 is substantially similar to catheter 300 and includes a catheter body 412 defining first and second lumens (not shown), at least two distal, normally closed one-way valves 418 and at least two proximal, normally closed one-way valves 420. As discussed above, at least one distal one-way valve 418 and one proximal one-way valve 420 communicates with each of the first and second lumens. In contrast to catheter 300, the proximal one-way valves 420 of catheter 400 are formed as flap valves which include a deformable rectangular flap 440 which deforms inwardly to facilitate fluid flow into a respective one of the lumens of the catheter body 412. As shown in FIG. 7, two flaps 440 may be provided to communicate with each of the first and second lumens. The flaps 440 may be secured to or integrally formed with the catheter body 412 along one inner wall 442 of each flap 440a. Alternatively, as shown in FIG. 7A, the flaps 440a may be secured to or integrally formed with the catheter body 412 along one outer wall 442a of each flap 440a. In another embodiment shown in FIG. 7B, the flaps 440a' are triangular in shape and are secured to or integrally formed with the catheter body 412 along a diagonal wall 442a'. Other flap configurations such as circular or oblong are envisioned.

Figure 8A:
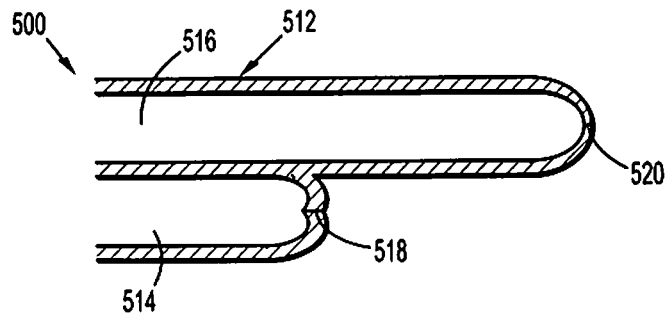
FIG. 8A is a longitudinal cross-sectional view of another embodiment of the presently disclosed valved tip catheter prior to use.
Figure 8B:
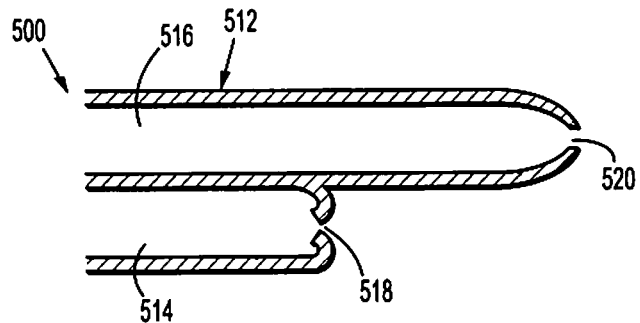
FIG. 8B is a cross-sectional view of the catheter shown in FIG. 8A in use.

FIGS. 8A and 8B illustrate another embodiment of the presently disclosed catheter shown generally as catheter 500. Catheter 500 is similar to the prior art catheter 10 shown in FIG. 1, but also includes one-way valves as will be discussed in further detail below. Catheter 500 includes a body 512 defining an arterial lumen 514 and a venous lumen 516. The body 512 defining the distal end of the venous lumen 516 extends distally beyond the distal end of the arterial lumen 514. The distal end of the arterial lumen 514 is sealed by an inwardly deformable one-way valve 518. Similarly, the distal end of the venous lumen 516 is enclosed by a outwardly deformable one-way valve 520. As illustrated, the thickness of the body 512 approaching the one-way valve 520 may become progressively thinner to facilitate operation of valve 520. When the catheter 500 is connected to a medical device, such as a dialyzer, fluid is withdrawn from a patient through the arterial lumen 514, delivered to the dialyzer for purification, and returned to the patient through the venous lumen 516. The one-way valves 518 and 520 open inwardly and outwardly, respectively, in response to a change in pressure within the arterial and venous lumens 514 and 516. During periods of non-use, such as during the period between dialysis treatments, valves 518 and 520 are normally closed to retain a lock solution, such as an anticoagulant, within the catheter lumens 514 and 516.

Referring also to FIGS. 8C-8G, one-way valves 518 and 520 prevent the use of catheter 500 in a reversible manner. More specifically, because one-way valve 520 only opens outwardly and one-way valve 518 only opens inwardly, the lumen 516 will only function as the venous lumen and the lumen 514 will only function as the arterial lumen. In order to ensure that the catheter 500 is properly connected to a medical device, a hub member 552 including a valve assembly 550 may be provided at a proximal end 502 of catheter body 512. In one embodiment, the valve assembly 550 includes two inwardly opening one-way valves 554 and two outwardly opening one-way valves 556. One side of each of the inwardly opening valves 554 communicates with a proximal end of the venous lumen 516 and one side of each of the outwardly opening one-way valves 556 communicates with the proximal end of the arterial lumen 514. In one embodiment, the hub member 552 communicates with extension tubes 570a and 570b. Each extension tube includes a connector 571 for connecting the respective extension tube 570a or 570b to a medical device such as a dialyzer. The extension tubes 570a and 570b connecting the proximal end 502 of the catheter 500 to the medical device (not shown) define two lumens 560 and 562, respectively. Lumen 560 which is provided for withdrawing fluid from the catheter 500 and delivering the fluid to a medical device, communicates with the other side of one of each of valves 554 and 556. Similarly, the lumen 562 is provided for supplying fluid to the catheter 500 from the medical device and communicates with the other side of one of each of valves 554 and 556.

In use, withdrawal lumen 560 is in fluid communication with one of valves 554 and one of valves 556 and supply lumen 562 is in communication with the other one of valves 554 and valves 556. Thus, when fluid is supplied through supply lumen 562 of extension tube 570b to the catheter 500, the inwardly opening valve 554 communicating with the venous lumen 516 of catheter body 512 will open to enable fluid to enter the venous lumen 516 only. Similarly, when fluid is withdrawn through withdrawal lumen 560 of extension tube 570a, the outwardly opening valve 556 communicating with the arterial lumen 514 of catheter body 512 will open to enable fluid to exit from the arterial lumen 514 only into the withdrawal lumen 560 of extension tube 570a. If, due to clinician error, the conduit 570 is incorrectly secured to the medical device, the valve assembly 550 will ensure fluid flow to and from the catheter 500 will occur along the desired arterial and venous lumens 514 and 516 of catheter body 512.

Figure 8G:
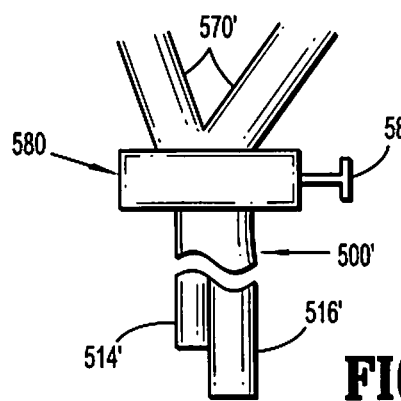
FIG. 8G is a top view of an alternate embodiment of the catheter assembly shown in FIG. 8C.

Referring to FIG. 8G, valve assembly 550 may be replaced with a manually operated spool valve 580 which can be manually actuated to ensure that fluid flow to and from the medical device is directed to the appropriate arterial and venous lumens 514' and 516' of the catheter 500'. Thus, even if conduits 570' are incorrectly attached to a medical device by a clinician, the spool valve 580 can be manually operated to supply fluid from the medical device to the venous lumen and withdraw fluid from the arterial lumen of the catheter 500'. Spool valve 580 may also include a flush port 584 in fluid communication with the arterial lumen 514' of the catheter 500' to facilitate flushing of the arterial lumen 514'. To further facilitate flushing of the arterial lumen 514', valve 518 may be configured to open outwardly under elevated pressures to enable the flush solution to expel any remaining blood within the arterial lumen 514'.

Figure 9:
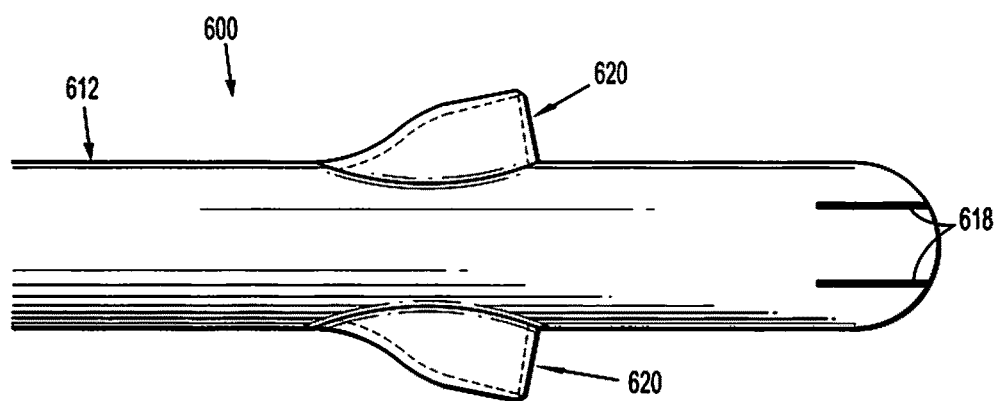
FIG. 9 is a top view of yet another embodiment of the presently disclosed valved tip catheter.

FIG. 9 illustrates yet another embodiment of the presently disclosed catheter shown generally as catheter 600. Catheter 600 is similar to catheters 100-400 and includes a catheter body 612 defining a first lumen, a second lumen, at least two distal outwardly openable one-way valves 618 and a pair of proximally positioned one-way duckbill valves 620. The first and second lumens each communicate with one of the distal one-way valves 618 and one of the proximal one-way duckbill valves 620. Catheter 600 operates in the same manner as catheters 100-400. More particularly, when catheter 600 is connected to a medical device, such as a dialyzer, fluid is withdrawn from a patient through one of the first and second lumens through one of the proximal inwardly openable duckbill valves 620 and returned to the patient through the other of the first and second lumens through one of the distal outwardly openable one-way valves 618. The distal and proximal one-way valves 618 and 620 are normally closed and moveable or deformable to the open position due to a change in pressure within the first and second lumens. As discussed above with respect to catheters 100-400, catheter 600 is reversible so that either of the first and second lumens can function as the arterial or venous lumen of the catheter. In addition, the normally closed distal and proximal one-way valves 618 and 620 maintain a lock solution, such as anticoagulant, within the first and second lumens during periods of non-use of catheter 600.

Figure 10:
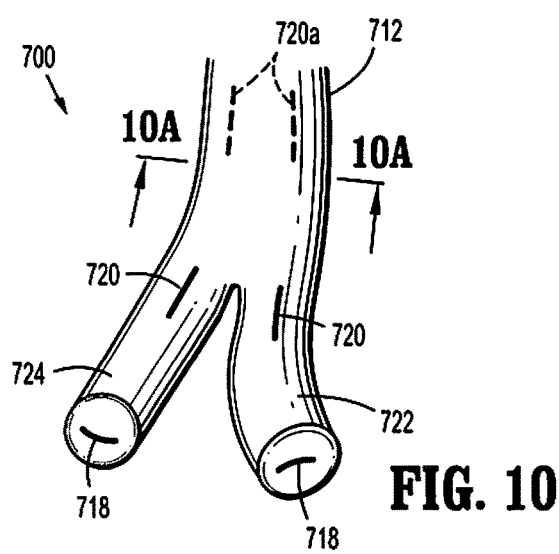
FIG. 10 is a perspective view of yet another embodiment of the presently disclosed valved tip catheter.
Figure 10A:
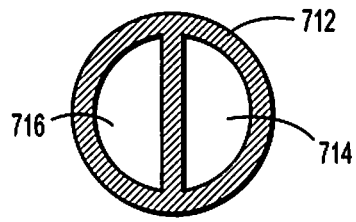
FIG. 10A is a cross-sectional view taken along section lines 10A-10A of FIG. 11.

Referring to FIGS. 10 and 10A, the above-described catheter features may also be incorporated within a split-tip catheter, shown generally as catheter 700. Catheter 700 includes a catheter body 712 which defines first and second lumens 714 and 716, and first and second separated distal tip portions 722 and 724. Each distal tip portion 722 and 724 defines a lumen which communicates with one of the first and second lumens 714 and 716 and includes a distal one-way valve 718 and a proximal one-way valve 720. The distal and proximal one-way valves 718 and 720 function as described above with respect to catheters 100-400 and 600 and will not be described further herein. In an alternate embodiment, the proximal one-way valves 720a can be formed (as shown in phantom in FIG. 9) in the catheter body 712 proximally of the separated tip portions 722 and 724.

Figure 11A:
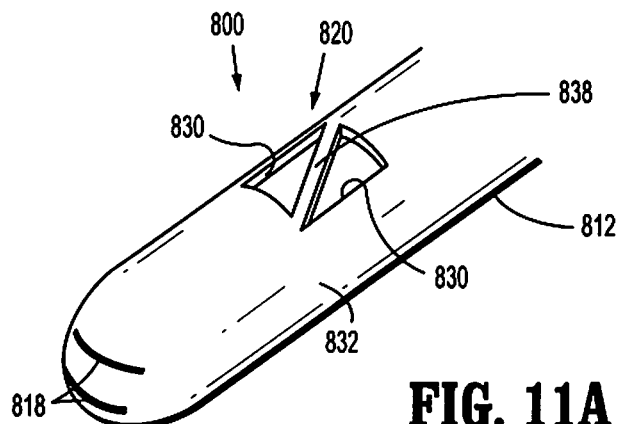
FIG. 11A is a perspective view of another embodiment of the presently disclosed valved tip catheter.
Figure 11B:
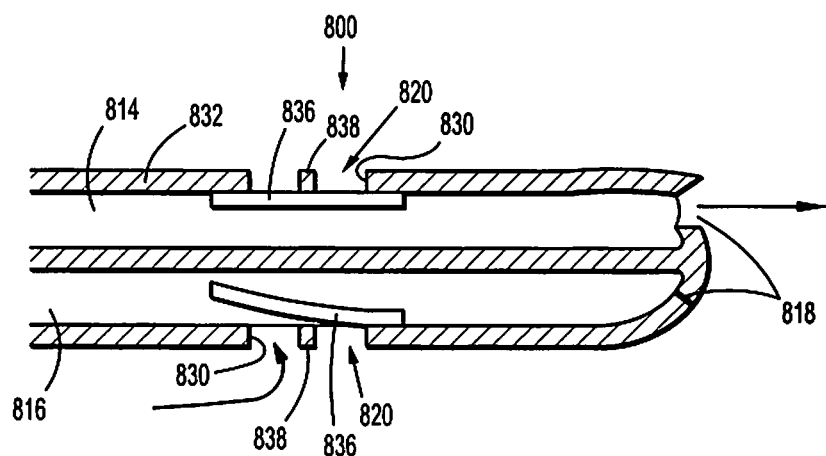
FIG. 11B is a longitudinal cross-sectional view of the catheter shown in FIG. 11A during use of the catheter.

FIGS. 11A-11B illustrate another embodiment of the presently disclosed catheter shown generally as catheter 800. Catheter 800 includes a body 812 defining first and second lumens 814 and 816, a pair of distal one-way valves 818 and a pair of proximal one-way valves 820. Catheter 800 is substantially similar to catheters 100-400 except that the proximal one-way valves 820 are configured differently. More specifically, each of the proximal valves 820 includes a throughbore 830 formed through a sidewall 832 of body 812 which is covered by a membrane 836. At least a portion of a periphery of membrane 836 is secured to an inner wall of body 812 using, for example, adhesives, welding or the like. A support rib 838 can be provided to add stability to the membrane 836 and can be integrally formed with body 812 to extend across the throughbore 830 to provide outward support for the membrane 836.

In use, when a negative pressure is created within one of the first or second lumens 814 or 816, the portion of the membrane 836 not secured to an inner wall of body 812 moves inwardly to enable fluid to enter the respective lumen 814 or 816 of the catheter 800. The distal one-way valves 818 function as described above with respect to distal one-way valves 118, 218, 318 and 418 and will not be described in further detail herein.

Figure 12A:
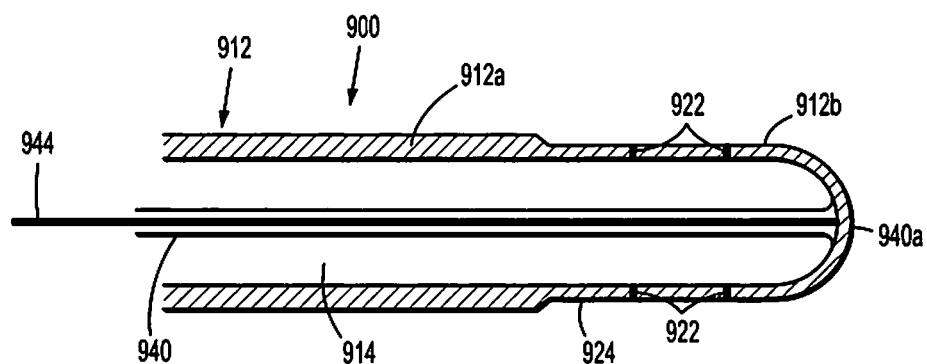
FIG. 12A is a cross-sectional view of another embodiment of the presently disclosed valved tip catheter.
Figure 12B:
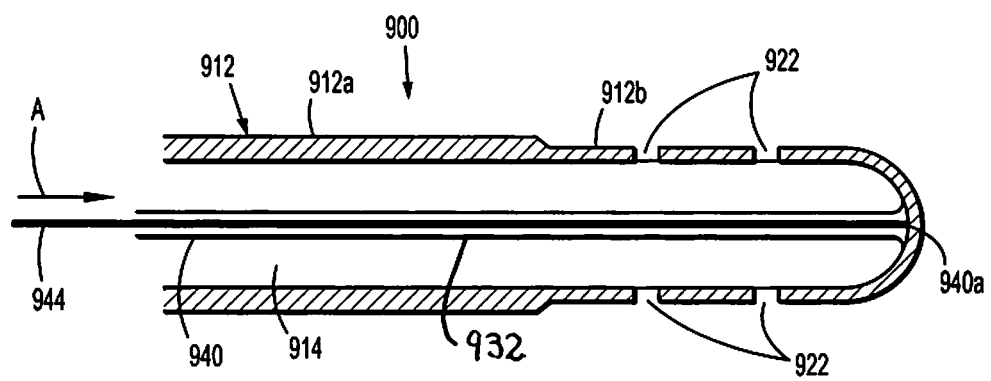
FIG. 12B is a cross-sectional view of the catheter shown in FIG. 12A in an open position.

FIGS. 12A-12B illustrate yet another embodiment of the presently disclosed catheter shown generally as catheter 900. Catheter 900 includes a catheter body 912 defining first and second lumens 914 and 916 Catheter body 912 includes a proximal body portion 912a formed of a material of standard durometer suitable for a catheter application, such as but not limited to 60A to 72D, or more specifically 75A to 55D, or even more specifically 80A to 90A, and a distal body portion 912b that may be formed of a more elastomeric material or configuration. Proximal and distal body portions 912a and 912b can be molded together as an integral structure or formed separately and joined together using known fastening techniques including adhesives or welding. One or more perforations 922 are formed through a sidewall 924 of the distal body portion 912b. In an unbiased state of the distal body portion 912b, the one or more perforations 922 are sealed due to the elastic nature of the distal body portion 912b.

Catheter body 912 includes a central channel 940 which extends along the first and second lumens 914 and 916 and includes a closed distal end 940a. Specifically, the central channel 940 may extend through a septum 932 separating the first and second lumens 914 and 916. A push rod 944 is slidably positioned within channel 940 and is movable in the direction indicated by arrow A in FIG. 12B from a retracted position shown in FIG. 12A to an extended position shown in FIG. 12B. In the extended position, the push rod 944 presses against the closed distal end 940a of channel 940 to stretch the elastomeric distal body portion 912b and open the perforations 922. When the push rod 944 is returned to its retracted position (FIG. 12A), the elastomeric distal body portion 912b returns to its unbiased state to close the perforations 922. Although not shown, two push rods 944 may be provided in a dual lumen catheter to facilitate manual opening of perforations 922 associated with each lumen independently. Alternatively, the push rod may extend within a channel formed along the septum within one of the lumens of a dual lumen catheter. Further still, the central channel 940 may be a single column running through a lumen in a single lumen catheter, such as a urinary catheter.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:
1. A split-tip catheter comprising:
a body defining first and second lumens and first and second separated distal tip portions, each of the separated distal tip portions defining a lumen which communicates with one of the first or second lumens, each of the separated distal tip portions including at least one distally located normally closed, one-way valve, each of the distally located one-way valves being configured to open in response to an increase in pressure within a respective one of the first and second lumens to enable fluid to be discharged from the respective first or second lumen;

at least one proximally located normally closed, one-way valve associated with each of the first and second lumens, each of the proximally located one-way valves being spaced proximally of the distally located one-way valves and being configured to open in response to a decrease in pressure within a respective one of the first and second lumens to enable fluid to enter the respective first or second lumen; and a support structure formed in the body adjacent at least one of the proximally located, one-way valves.

2. The catheter according to claim 1, wherein each of the distally located one-way valves is a slit valve.

3. The catheter according to claim 2, wherein each of the proximally located one-way valves is a slit valve.

4. The catheter according to claim 1, wherein each of the proximally located one-way valves includes a slit which extends through the body and a concavity formed about the slit.

5. The catheter according to claim 4, wherein the at least one proximally located one-way valve includes two proximally located one-way valves associated with a respective one of each of the first and second lumens.

6. The catheter according to claim 1, wherein each of the proximally located one-way valves is a flap-valve, the flap valve including a deformable flap.

7. The catheter according to claim 6, wherein the deformable flap is rectangular.

8. The catheter according to claim 6, wherein the flap is triangular.

9. The catheter according to claim 1, wherein each of the proximally located one-way valves is a duckbill valve.

10. The catheter according to claim 1, wherein each of the separated distal tip portions include at least one of the proximally located one-way valves.

11. The catheter according to claim 1, wherein at least one of the proximally located one-way valves is formed in the body proximally of the separated distal tip portions.

12. The catheter according to claim 1, wherein each of the proximally located one-way valves includes a membrane supported within the respective one of the first and second lumens of the body, the membrane being positioned to cover a throughbore formed in the body and being inwardly movable to enable fluid to enter the throughbore, at least a portion of the membrane being secured to the body.

13. The catheter according to claim 12, further including a support rib extending across the throughbore, the support rib being positioned to prevent outward movement of the membrane.

14. A split-tip catheter comprising:
a body defining first and second lumens and first and second separated distal tip portions, each of the separated distal tip portions defining a lumen which communicates with one of the first or second lumens, each of the separated distal tip portions including at least one distally located normally closed, one-way valve, each of the distally located one-way valves being configured to open in response to an increase in pressure within a respective one of the first and second lumens to enable fluid to be discharged from the respective first or second lumen; and at least one proximally located normally closed, one-way valve associated with each of the first and second lumens, each of the proximally located one-way valves being spaced proximally of the distally located one-way valves and being configured to open in response to a decrease in pressure within a respective one of the first and second lumens to enable fluid to enter the respective first or second lumen, wherein each of the proximally located one-way valves includes tapered inwardly deformable flaps.

15. A split-tip catheter comprising:
a body defining a venous lumen, an arterial lumen and first and second separated distal tip portions, the first distal tip portion defining a first lumen which communicates with the venous lumen and the second distal tip portion defining a second lumen which communicates with the arterial lumen, a distal end of the first distal tip portion extending distally beyond a distal end of the second distal tip portion;

a one-way valve formed in the first distal tip portion and configured to enable fluid to be discharged from the venous lumen upon an increase in pressure within the venous lumen;

a one-way valve formed in the second distal tip portion and configured to enable fluid to enter the arterial lumen upon a decrease in pressure within the arterial lumen; and a support structure formed in the body adjacent at least one of the one-way valves.

16. The catheter according to claim 15, further comprising a catheter hub having a first end secured to a proximal end of the body, the catheter hub supporting a valve assembly having two inlet one-way valves which communicate with the venous lumen and enable fluid to flow into the venous lumen and two outlet one-way valves which communicate with the arterial lumen and enable fluid to flow from the arterial lumen.

17. The catheter according to claim 16, further comprising a conduit defining first and second lumens and having a first end connected to a second end of the catheter hub such that each of the first and second lumens communicates with one of the inlet one-way valves and one of the outlet one-way valves.

18. The catheter according to claim 17, wherein the conduit is adapted to communicate with a medical device.

19. A split-tip catheter comprising:
a body defining first and second lumens and first and second separated distal tip portions, each of the separated distal tip portions defining a lumen which communicates with one of the first and second lumens;

at least one distally located normally closed, one-way valve in fluid communication with at least one of the first and second lumens, each of the distally located one-way valves being configured to open in response to an increase in pressure within the respective first and second lumens to which the distally located one-way valve is in fluid communication to enable fluid to be discharged from the respective first or second lumen; and at least one proximally located normally closed, one-way valve in fluid communication with at least one of the first and second lumens, each of the proximally located one-way valves being spaced proximally of the distally located one-way valves and being configured to open in response to a decrease in pressure within the respective first and second lumens to which the proximally located one-way valve is in fluid communication to enable fluid to enter the respective first or second lumen; and a support structure formed in the body adjacent at least one of the proximally located, one-way valves.

* * * * *